(12) United States Patent
Kostansek et al.

(10) Patent No.: US 8,541,344 B2
(45) Date of Patent: *Sep. 24, 2013

US008541344B2

(54) COMPOSITIONS WITH CYCLOPROPENES AND METAL-COMPLEXING AGENTS

(75) Inventors: Edward Charles Kostansek, Buckingham, PA (US); Bridget Marie Stevens, Horsham, PA (US)

(73) Assignee: Rohm and Haas Company, Indianapolis, IN (US)

( * ) Notice: Subject to any disclaimer, the term of this patent is extended or adjusted under 35 U.S.C. 154(b) by 1074 days.

This patent is subject to a terminal disclaimer.

(21) Appl. No.: 11/131,615

(22) Filed: May 18, 2005

(65) Prior Publication Data

US 2005/0261132 A1    Nov. 24, 2005

Related U.S. Application Data

(60) Provisional application No. 60/572,742, filed on May 19, 2004.

(51) Int. Cl.
*A01N 27/00*    (2006.01)
*A01N 25/28*    (2006.01)

(52) U.S. Cl.
USPC .......................................... 504/357; 504/359

(58) Field of Classification Search
USPC ................................................. 504/357, 359
See application file for complete search history.

(56) References Cited

U.S. PATENT DOCUMENTS

| | | | |
|---|---|---|---|
| 4,191,551 | A | 3/1980 | Cupery |
| 5,123,951 | A | 6/1992 | See et al. |
| 5,219,825 | A | 6/1993 | Gressel et al. |
| 5,518,988 | A | 5/1996 | Sisler et al. |
| 6,017,849 | A * | 1/2000 | Daly et al. .................... 504/114 |
| 6,313,068 | B1 | 11/2001 | Daly |
| 6,426,319 | B1 * | 7/2002 | Kostansek .................... 504/357 |
| 6,444,619 | B1 | 9/2002 | Kostansek |
| 6,706,666 | B2 | 3/2004 | Hasebe et al. |
| 6,762,153 | B2 | 7/2004 | Kostansek et al. |
| 6,897,185 | B1 | 5/2005 | Chang |
| 2001/0019995 | A1 | 9/2001 | Sisler |
| 2003/0055010 | A1 | 3/2003 | De Haan |
| 2003/0224939 | A1 | 12/2003 | Miles |
| 2004/0014736 | A1 | 1/2004 | El A'mma et al. |
| 2004/0082480 | A1 | 4/2004 | Daly et al. |
| 2004/0249079 | A1 * | 12/2004 | Funk et al. .................... 525/191 |
| 2007/0093389 | A1 | 4/2007 | Rademacher et al. |

FOREIGN PATENT DOCUMENTS

| | | |
|---|---|---|
| CN | 1433301 | 3/2002 |
| EP | 1 340 425 | 5/2005 |
| WO | WO 01/43548 | 6/2001 |
| WO | WO 02/24171 | * 3/2002 |
| WO | WO 2004/101668 | 11/2004 |

OTHER PUBLICATIONS

Sinex, S. A. (EDTA—Mar. 1, 2004).*
General Safety (Apr. 15, 1998).*
Drinking Water Contaminants—Copper (obtained via http://www.freedrinkingwater.com/water-contamination/copper-contaminants-removal-water.htm, dated on Sep. 28, 2012).*
K. C. Bishop, "Transition Metal Catalyzed Rearrangements of Small Ring Organic Molecules," Chemical Reviews, 1976, vol. 76, No. 4, pp. 461-486.
R.E. Byers, et.al., "Pre Harvest Fruit Drop, Harvest Quality, and Cold Storage of 'Golden Delicious' and 'Rome' Apples," Proceedings of the Plant Growth Regulation Society of America, v.27, pp. 175-180, 2000.
R. Beaudry "Small batch 1-MCP (SmartFresh) applications", Integrated Pest Management Resources, vol. 22, No. 16, Aug. 21, 2007, pp. 2-3.
Rohm and Haas Company, "SmartFresh™ SmartTabs Material Safety Data Sheet," Apr. 30, 2002.
G. Regiroli, "Introducing SmartFresh™ (1-methylcyclopropene)," World Avocado Conference V, 2003, A-83 pp. 216-217.
Taimir-Riahi HA, "Interaction of D-glucose with alkaline-earth metal ions. Syntheis, spectroscopic, and . . . ," Carbohyrate Research, vol. 183, pp. 35-46, 1988 (abstract).
Yano, et al., "Interactions between metal ions and simple sugars: Main . . . ," excerpt from Metal Ions in Biological Systems, (ed. A. Sigel and M. Sigel) vol. 32, 1966, pp. 42-44.
E. Norkus, "Interaction of beta-Cyclodextrin with cadmium(II) ions," International Journal of Biological MacromOlecules, vol. 33, p. 251-254, 2003.
Fuchs, et. al., "Multinuclear Sandwich-type Complexes of Deprotonated beta-yclodextrin and Copper (II) Ions," Agnew. Chem. Int. Ed. Engl., vol. 32, No. 6, pp. 852-854, 1993.
Y. Matsui, et. al., "Complexee.Of Copper (II) with Cyclodextrins," Bulletin of the Chemical Society of Japan, vol. 45, No. 10, p. 3229, Oct. 1972.
Z. El Rassi, "Capillary Electrophoresis of Carbohydrates," in Advances in Chromatography, vol. 34, edited by R. Brown et. al., CRC Press, 1994.
Wikipedia, "Cyclodextrin," http://en.wikipedia.org/wiki/Cyclodextrin, Apr. 11, 2009.
Rohm and Haas Company, "EthylBloc™ Technology Material Safety Data Sheet," Oct. 4, 2001.
L. Pozo, "Differential Effects of 1-Methylcyclopropene on Citrus Leaf and Mature Fruit Abscission," Journal American Horticulture Society, vol. 129, No. 4, pp. 473-478, 2004.

* cited by examiner

*Primary Examiner* — Mina Haghighatian
*Assistant Examiner* — Helen Chui
(74) *Attorney, Agent, or Firm* — Yung H. Lee; TraskBritt P.C.

(57) ABSTRACT

A composition is provided that contains a cyclopropene and a metal-complexing agent. Also provided is a method that includes contacting such compositions to plants or plant parts.

22 Claims, No Drawings

COMPOSITIONS WITH CYCLOPROPENES AND METAL-COMPLEXING AGENTS

This application claims the benefit of U.S. Provisional Application No. 60/572,742, filed May 19, 2004.

BACKGROUND

Ethylene can cause the premature death of plants or plant parts including, for example, flowers, leaves, fruits, and vegetables through binding with certain receptors in the plant. Ethylene also promotes leaf yellowing and stunted growth as well as premature fruit, flower, and leaf drop. Cyclopropenes (i.e., substituted and unsubstituted cyclopropene and its derivatives) are effective agents for blocking the effects of ethylene. Some useful methods of delivering cyclopropenes to plants or plant parts include forming a mixture that includes one or more cyclopropenes and water. However, in some of such mixtures, the activity of the cyclopropenes in the mixture is reduced. U.S. 2003/0224939 discloses the use of permeabilizing agents to improve the permeability of the cell walls of plants to certain specific plant growth regulators. It is desired to provide improved compositions that contain cyclopropenes and that improve the activity of cyclopropenes in mixtures that contain water and one or more such improved compositions; it is also desired to improve the effectiveness of blocking the effects of ethylene by cyclopropenes that are delivered to plants or plant parts by methods that use such compositions.

STATEMENT OF THE INVENTION

In the present invention, there is provided a composition comprising
(a) one or more cyclopropenes of the formula

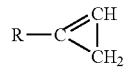

wherein said R is hydrogen or a substituted or unsubstituted alkyl, alkenyl, alkynyl, cycloalkyl, cycloalkylalkyl, phenyl, or naphthyl group; wherein the substituents, when present, are independently halogen, alkoxy, or substituted or unsubstituted phenoxy; and,
(b) one or more metal-complexing agents.

DETAILED DESCRIPTION

As used herein, all percentages are percent by weight and all parts are parts by weight, unless otherwise specified, and are inclusive and combinable. All ratios are by weight and all ratio ranges are inclusive and combinable. All molar ranges are inclusive and combinable.

As used herein, the term "alkyl" means straight chain, branched chain, or cyclic ($C_1$-$C_{20}$) radicals which include, for example, methyl, ethyl, n-propyl, isopropyl, 1-ethylpropyl, n-butyl, tert-butyl, isobutyl, 2,2-dimethylpropyl, pentyl, octyl, and decyl. The terms "alkenyl" and "alkynyl" mean ($C_3$-$C_{20}$) alkenyl and ($C_3$-$C_{20}$) alkynyl groups such as, for example, 2-propenyl, 2-butenyl, 3-butenyl, 2-methyl-2-propenyl, and 2-propynyl. The term "cycloalkylalkyl" means a ($C_1$-$C_{15}$) alkyl group substituted with a ($C_3$-$C_7$) cycloalkyl group such as, for example cyclopropylmethyl, cyclopropylethyl, cyclobutylmethyl, and cyclopentylethyl. The term "haloalkyl" means an alkyl radical wherein one or more of the hydrogen atoms have been replaced by a halogen atom. The term "halogen" means one or more of fluorine, chlorine, bromine, and iodine.

The practice of the present invention involves the use of one or more cyclopropenes. As used herein, "cyclopropene" means any compound with the formula

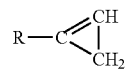

where R is hydrogen or a substituted or unsubstituted alkyl, alkenyl, alkynyl, cycloalkyl, cycloalkylalkyl, phenyl, or naphthyl group; wherein the substituents, when present, are independently halogen, alkoxy, or substituted or unsubstituted phenoxy. As used herein, when the compound of the above structure when R is a hydrogen is meant, the phrase "unsubstituted cyclopropene" will be used.

In some embodiments, R has no double bond. Independently, in some embodiments, R has no triple bond. Independently, in some embodiments, there is no halogen atom substituent on R. Independently, in some embodiments, R has no substituents that are ionic. Independently, in some embodiments, R is not capable of generating oxygen compounds.

In some embodiments of the invention, R is ($C_1$-$C_{10}$) alkyl. In some embodiments, R is ($C_1$-$C_8$) alkyl, or ($C_1$-$C_4$) alkyl, or methyl. When R is methyl, the cyclopropene is known herein as "1-MCP."

The cyclopropenes applicable to this invention are known materials, which may be prepared by any method. Some suitable methods of preparation of cyclopropenes are the processes disclosed in U.S. Pat. Nos. 5,518,988 and 6,017,849.

The amount of cyclopropene in compositions of the present invention may vary widely, depending on the type of composition and the intended method of use. In some embodiments, the amount of cyclopropene, based on the total weight of the composition, is 4% by weight or less; or 1% by weight or less; or 0.5% by weight or less; or 0.05% by weight or less. Independently, in some embodiments, the amount of cyclopropene, based on the total weight of the composition, is 0.000001% by weight or more; or 0.00001% by weight or more; or 0.0001% by weight or more; or 0.001% by weight or more.

Among embodiments in which the composition of the present invention includes water, the amount of cyclopropene may, in some embodiments that include water, be characterized as parts per million (i.e., parts by weight of cyclopropene per 1,000,000 parts by weight of water, "ppm") or as parts per billion (i.e., parts by weight of cyclopropene per 1,000,000,000 parts by weight of water, "ppb"). In some embodiments that include water, the amount of cyclopropene is 1 ppb or more; or 10 ppb or more; or 100 ppb or more. Independently, in some embodiments that include water, the amount of cyclopropene is 10,000 ppm or less; or 1,000 ppm or less.

The practice of the present invention involves the use of one or more metal-complexing agents. A metal-complexing agent is a compound that contains one or more electron-donor atoms capable of forming coordinate bonds with a metal atoms. Some metal-complexing agents are chelating agents. As used herein, a "chelating agent" is a compound that contains two or more electron-donor atoms that are capable of forming coordinate bonds with a metal atom, and a single molecule of the chelating agent is capable of forming two or more coordinate bonds with a single metal atom. Suitable chelating agents include, for example, organic and inorganic chelating agents. Among the suitable inorganic chelating agents are, for example, phosphates such as, for example, tetrasodium pyrophosphate, sodium tripolyphosphate, and hexametaphosphoric acid. Among the suitable organic chelating agents are those with macrocyclic structures and non-macrocyclic structures. Among the suitable macrocyclic organic chelating agents are, for example, porphine compounds, cyclic polyethers (also called crown ethers), and macrocyclic compounds with both nitrogen and oxygen atoms.

Some suitable organic chelating agents that have non-macrocyclic structures are, for example, aminocarboxylic acids, 1,3-diketones, hydroxycarboxylic acids, polyamines, aminoalcohols, aromatic heterocyclic bases, phenol, aminophenols, oximes, Shiff bases, sulfur compounds, and mixtures thereof. In some embodiments, the chelating agent includes one or more aminocarboxylic acids, one or more hydroxycarboxylic acids, one or more oximes, or a mixture thereof. Some suitable aminocarboxylic acids include, for example, ethylenediaminetetraacetic acid (EDTA), hydroxyethylethylenediaminetriacetic acid (HEDTA), nitrilotriacetic acid (NTA), N-dihydroxyethylglycine (2-HxG), ethylenebis(hydroxyphenylglycine) (EHPG), and mixtures thereof. Some suitable hydroxycarboxylic acids include, for example, tartaric acid, citric acid, gluconic acid, 5-sulfosalicylic acid, and mixtures thereof. Some suitable oximes include, for example, dimethylglyoxime, salicylaldoxime, and mixtures thereof. In some embodiments, EDTA is used.

Some additional suitable chelating agents are polymeric. Some suitable polymeric chelating agents include, for example, polyethyleneimines, polymethacryloylacetones, poly(acrylic acid), and poly(methacrylic acid). Poly(acrylic acid) is used in some embodiments.

Some suitable metal-complexing agents that are not chelating agents are, for example, alkaline carbonates, such as, for example, sodium carbonate.

Metal-complexing agents may be present in neutral form or in the form of one or more salts. Mixtures of suitable metal-complexing agents are also suitable.

In some embodiments, the composition of the present invention includes water. Independently, the composition of the present invention, whether or not it contains water, may, in some embodiments, be used in methods that include admixing the composition of the present invention with water. Whether the water is included in the composition of the present invention or the water is mixed with the composition of the present invention, the water that is used may suitably come from any source. Suitable water may be, for example, purified or unpurified. Suitable purified water may be, for example, deionized or distilled or both. Suitable unpurified water may be from any source, including, for example, municipal water supplies, wells, streams, other natural sources, irrigation ditches, or any combination thereof.

In some embodiments in which water is used, the water contains one or more metal ions, such as, for example, iron ions, copper ions, other metal ions, or mixtures thereof. In some embodiments, the water contains 0.1 ppm or more of one or more metal ions.

While the present invention is not limited to any particular mechanism, it is contemplated that metal ions, in some cases, interact with cyclopropene in a way that reduces the activity of cyclopropene. In such cases, it is further contemplated that a metal-complexing agent may interact with metal ion in a way the reduces the interaction between metal ion and cyclopropene, thus preserving the activity of cyclopropene.

The amount of metal-complexing agent used in the present invention also may vary widely. In some embodiments, the amount of metal-complexing agent will be adjusted to be sufficient to complex the amount of metal ion that is present or expected to encounter. Metal-complexing agent might, for example, encounter metal ion in the composition of the present invention, in the admixture formed when the composition of the present invention is admixed with water, or both. For example, in some embodiments, if a relatively efficient chelating agent is used as a metal-complexing agent (i.e., a chelating agent that will form a complex with all or nearly all the metal ions in the water), the ratio of moles of chelating agent to moles of metal ion will be 0.1 or greater; or 0.2 or greater; or 0.5 or greater; or 0.8 or greater. Among such embodiments that use a relatively efficient chelating agent, the ratio of moles of chelating agent to moles of metal ion will be 2 or less; or 1.5 or less; or 1.1 or less.

Independently, in some embodiments, the amount of metal-complexing agent is, based on the total weight of the composition, 25% by weight or less; or 10% by weight or less; or 1% by weight or less. Independently, in some embodiments, the amount of metal-complexing agent is, based on the total weight of the composition, 0.00001% or more; or 0.0001% or more; or 0.01% or more.

Independently, in some of the embodiments in which the composition of the present invention includes water, the amount of metal-complexing agent can usefully be determined by the molar concentration of metal-complexing agent in the water. In some embodiments, the concentration of metal-complexing agent is 0.00001 mM (i.e., milli-Molar) or greater; or 0.0001 mM or greater; or 0.001 or greater; or 0.01 or greater; or 0.1 or greater. Independently, in some embodiments, the concentration of metal-complexing agent is 100 mM or less; or 10 mM or less; or 1 mM or less.

In some embodiments, the composition includes at least one molecular encapsulating agent. Useful molecular encapsulating agents include, for example, organic and inorganic molecular encapsulating agents. Suitable organic molecular encapsulating agents include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In some embodiments of the invention, the encapsulating agent is α-cyclodextrin ("α-CD"), β-cyclodextrin, γ-cyclodextrin, or a mixture thereof. In another embodiment of the invention, particularly when the cyclopropene is 1-methylcyclopropene, the encapsulating agent is α-cyclodextrin. The preferred encapsulating agent will vary depending upon the size of the R group. However, as one skilled in the art will appreciate, any cyclodextrin or mixture of cyclodextrins, cyclodextrin polymers, modified cyclodextrins, or mixtures thereof can also be utilized pursuant to the present invention. Cyclodextrins are available from Wacker Biochem Inc., Adrian, Mich. or Cerestar USA, Hammond, Ind., as well as other vendors.

Among embodiments of the present invention in which a molecular encapsulating agent is used, it is contemplated that, in some embodiments, the composition includes at least one molecular encapsulating agent that encapsulates one or more cyclopropenes. A cyclopropene or substituted cyclopropene molecule encapsulated in a molecule of a molecular encapsulating agent is known herein as a "cyclopropene molecular encapsulating agent complex." The cyclopropene molecular encapsulation agent complexes, when used in the present invention, can be prepared by any means. In one method of preparation, for example, such complexes are prepared by contacting the cyclopropene with a solution or slurry of the molecular encapsulation agent and then isolating the complex, again using general processes disclosed in U.S. Pat. No.

6,017,849. In the case of 1-MCP, the 1-MCP gas is bubbled through a solution of α-cyclodextrin in water, from which the complex first precipitates and is then isolated by filtration.

Among embodiments of the present invention in which a molecular encapsulating agent is used, in some of such embodiments, the amount of molecular encapsulating agent can usefully be characterized by the ratio of moles of molecular encapsulating agent to moles of cyclopropene. In some of such embodiments, the ratio of moles of molecular encapsulating agent to moles of cyclopropene is 0.1 or larger; or 0.2 or larger; or 0.5 or larger; or 0.9 or larger. Independently, in some of such embodiments, the ratio of moles of molecular encapsulating agent to moles of cyclopropene is 2 or lower; or 1.5 or lower.

It is sometimes desirable to include in the composition one or more adjuvants, such as, for example, extenders, pigments, fillers, binders, plasticizers, lubricants, surfactants, wetting agents, spreading agents, dispersing agents, stickers, adhesives, defoamers, thickeners, transport agents, and emulsifying agents. Some of such adjuvants commonly used in the art can be found in the John W. McCutcheon, Inc. publication *Detergents and Emulsifiers, Annual*, Allured Publishing Company, Ridgewood, N.J., U.S.A. In some embodiments, the composition includes one or more surfactants. In some embodiments, the compositions includes one or more anionic surfactants. Independently, in some embodiments, the composition includes one or more alkyl alcohols. In some embodiments, the composition includes one or more alkyl alcohols where the alkyl group has 6 or fewer carbon atoms, or 3 or fewer carbon atoms.

One useful method of assessing the usefulness of compositions is the activity of the composition. As used herein, "activity" of a cyclopropene means the concentration of pure cyclopropene that is available to be used. For example, in general, if a reagent is mixed with a composition containing cyclopropene, and that reagent reacts with some or all of the cyclopropene, or that reagent complexes with some or all of the cyclopropene in a way that makes some or all of the cyclopropene undetectable or unavailable for useful purposes, that reagent is said to reduce the activity of the cyclopropene. One method of measuring the activity of a composition of the present invention is by analyzing the cyclopropene concentration in the headspace above a sample of the composition, for example by using the headspace measurement method defined herein below. Another method of measuring the activity of a composition of the present invention is by testing the effectiveness of the composition in treating plants, using methods, for example, like the tomato epinasty test defined herein below.

The ingredients of the present invention may be admixed by any means, in any order. In some embodiments in which the composition of the present invention includes water, the metal-complexing agent is admixed with the water before the water and the cyclopropene come into contact. In some of such embodiments, the metal-complexing agent and the cyclopropene contact the water at the same time. In some of such embodiments, the cyclopropene and the water come into contact with each other before the metal-complexing agent is admixed with the water; such embodiments are contemplated to be useful as long as the cyclopropene has some useful level of activity at the time when the metal-complexing agent is admixed with the water. Also contemplated are embodiments in which metal-complexing agent is admixed with cyclopropene to form a composition of the present invention; such a composition of the present invention may, if desired, then be admixed with water.

Among embodiments in which a molecular encapsulating agent is used, the ingredients may be admixed by any means, in any order. In some embodiments, a cyclopropene molecular encapsulating agent complex is made. In some embodiments, a cyclopropene molecular encapsulating agent complex is admixed with water, and the metal-complexing agent is added simultaneously or subsequently. In some embodiments, a cyclopropene molecular encapsulating agent complex is admixed with an admixture of water and metal-complexing agent. In some embodiments, cyclopropene molecular encapsulating agent complex and metal-complexing agent are admixed to form a composition of the present invention; such a composition of the present invention may, if desired then be admixed with water.

It is contemplated that combinations of the above embodiments are also possible; for example, some metal-complexing agent could be admixed with cyclopropene (with or without the presence of molecular encapsulating agent), while further metal-complexing agent could be admixed with water, and then the two admixtures could be admixed with each other.

It is further contemplated that the composition of the present invention may be in contact with water for a short time or a long time. For example, one embodiment is contemplated in which gaseous cyclopropene that is not highly soluble in water could be bubbled through water that contains metal-complexing agent. For another example, an embodiment is contemplated in which a cyclopropene molecular encapsulating agent complex is admixed with water that contains metal-complexing agent, and the admixture is then stored for a relatively long time.

It is to be understood that adjuvants, if used, may be added to any of the above admixtures or to other admixtures of ingredients or to a composition of the present invention.

For one example, in some embodiments, a composition of the present invention is made by admixing cyclopropene molecular encapsulating agent complex, metal-complexing agent, optionally one or more fillers, and, optionally other ingredients; such a composition could be, in some embodiments, stored and used at a later time. It is contemplated that such compositions of the present invention have little or no water. Depending on the choice of fillers, other ingredients, or both, it is contemplated that such compositions of the present invention could be a liquid, dispersion, paste, solid, powder, or combination thereof. It is contemplated that it may, in some cases, be desirable to use such a composition by admixing it with water and contacting the admixture to one or more plants or plant parts.

For an additional example, in some embodiments, an admixture of water and cyclopropene molecular encapsulating agent complex could made and stored; and when it is desired to use the composition, the powder and the admixture of water and metal-complexing agent could be admixed.

For another example, in some embodiments, an admixture is made of cyclopropene molecular encapsulating agent complex, metal-complexing agent, water, and at least one adjuvant selected from surfactants, alcohols, or a mixture thereof. Such an admixture could be stored for relatively long times before use; such admixtures are contemplated to be most useful in cases where the concentration of cyclopropene molecular encapsulating agent complex in water is relatively low. In some of such embodiments, the adjuvants used include at least one anionic surfactant or at least one alkyl alcohol or a mixture thereof.

In some embodiments, a composition of the present invention is used to treat plants or plant parts. Such treatment may be conducted by any method that allows cyclopropene to contact the plants or plant parts. Plant parts include any part of a plant, including, for example, flowers, blooms, seeds, cuttings, roots, bulbs, fruits, vegetables, leaves, and combinations thereof. In some embodiments, a composition of the present invention is used to treat one or more of blooms, fruits, and vegetables.

In some embodiments, the cyclopropene leaves the composition of the present invention and diffuses through air or other gas phase to contact the plant or plant part. In some embodiments, the composition of the present invention contacts the plant; such contact may be accomplished by any method. Some examples of methods of contact are, for example, spraying, foaming, fogging, pouring, brushing, dipping, similar methods, and combinations thereof. In some embodiments, spraying or dipping or both is used.

EXAMPLES

In the following examples, the examples marked with "(C)" are comparative examples.

Cyclopropene Headspace Measurement Method:

A composition containing water and cyclopropene was sealed in a bottle equipped with a septum in a manner that leaves a portion of the volume of the bottle filled with gas; a portion of the headspace was analyzed for cyclopropene at 1 hour after injection. The analysis method was gas chromatography using the following parameters:

| | |
|---|---|
| Instrument: | Hewlett Packard (Agilent Technologies) 6890 |
| Detector: | Flame Ionization |
| Detector Temperature: | 150 deg. C. |
| Air Flow Rate: | 450 ml/min. |
| Hydrogen Flow Rate: | 40 ml/min. |
| Make up Gas Flow Rate: | 25 ml/min. |
| Column: | Chrompack CP-PoraPlot Q-HT |
| Dimensions: | 10 m × 0.32 mm i.d. |
| Film Thickness: | 10 microns |
| Carrier Gas: | Helium |
| Flow Rate: | 2.5 ml/min |
| Column Head Pressure: | 6 psi |
| Injection Port Temperature: | 150 deg. C. |
| Initial Temperature: | 35 deg. C. |
| Initial Time: | 0.5 min. |
| Program Rate 1: | 20 deg. C./min. |
| Final Temperature: | 250 deg. C. |
| Final Time: | 6.5 min. |
| Injection Volume: | 1 ml |
| Injector: | Manual/Splitless (1 ml inlet glass liner) |

Cyclopropene Release Measurement

The release of cyclopropene from a mixture of water and cyclopropene was measured as follows. A sample of cyclopropene molecular encapsulating agent complex (0.02 g of complex containing 0.14% by weight, based on the weight of the complex, cyclopropene) was sealed into a bottle (122 ml volume) fitted with a septum, water (3 ml) was injected into the bottle, and the concentration of cyclopropene in the headspace was measured as described herein above.

From the measure concentration of cyclopropene in the headspace and the amount of cyclopropene added to the bottle, the fraction of the total amount of cyclopropene in the bottle that resides in the headspace can be calculated and reported as a percentage based on the amount of cyclopropene added to the bottle.

Example 1

Results of Cyclopropene Release Measurements

Samples were prepared as described in the Release Measurement Method described above, using 1-MCP and α-CD. Five different sources of water were used: two different tap waters, two different deionized waters, and filtered water (purified with a MilliQ™ purification system from Millipore). No metal-complexing agent was included. Results were as follows:

| Water Source | % Release of 1-MCP |
|---|---|
| tap #1 (C) | 60 |
| tap #2 (C) | 13 |
| deionized #1 (C) | 100 |
| deionized #2 (C) | 60 |
| filtered (C) | 100 |

Some sources of water reduce the activity of 1-MCP.

Example 2

Addition of Citric Acid

The results for tap #2 of Example 1 were repeated, with the difference that citric acid was first added to the water. Results were as follows:

| Concentration of Citric Acid (milliMolar) | % Release of 1-MCP |
|---|---|
| 100 | 92 |
| 10 | 100 |
| 1 | 63 |

The presence of citric acid improves the % release dramatically, compared to the 13% that occurred with no citric acid (Example 1).

Example 3

Addition of Sodium Salt of EDTA

The procedures of Example 2 were repeated using the sodium salt of EDTA instead of citric acid. Results were as follows:

| Concentration of Sodium Salt of EDTA (milliMolar) | % Release of 1-MCP |
|---|---|
| 10 | 100 |
| 1 | 100 |
| 0.1 | 100 |
| 0.01 | 100 |
| 0.001 | 100 |
| 0.0001 | 100 |
| 0.00001 | 87 |

The presence of sodium salt of EDTA improves the % release dramatically, compared to the 13% that occurred with no citric acid (Example 1).

Example 4

Effect of Added Copper Ion

The procedures of Example 1 were repeated. In this case, the water was deionized water #1 with added copper ion (added in the form of cupric sulfate). The results were as follows:

| Concentration of Copper Ions (parts per million) | Concentration of Sodium Salt of EDTA (milliMolar) | % Release of 1-MCP |
|---|---|---|
| 0 (C) | 0 | 100 |
| 10 (C) | 0 | 10 |
| 5 (C) | 0 | 36 |
| 1 (C) | 0 | 54 |
| 5 | 11 | 100 |
| 5 | 11[1] | 37 |

Note
[1] sodium salt of EDTA was added 2 hours after 1-MCP α-CD complex was admixed with water, and headspace was measured 1 hour later.

Presence of copper ions without sodium salt of EDTA causes reduction in activity of 1-MCP; sodium salt of EDTA, when added to the water before the 1-MCP α-CD complex was added to the water, maintains the full activity of the 1-MCP; sodium salt of EDTA, when added to water 2 hours after the 1-MCP α-CD complex was added to the water, fails to maintain the activity of the 1-MCP.

Example 5

Further Metal-Complexing Agents

The experiments of Example 4 were repeated, using 5 ppm (parts per million) of copper ion in every sample, and various types and amounts of metal-complexing agents, and the results were as follows. Concentration of meta-complexing agent is shown in mM (milliMolar):

| Metal-Complexing Agent | Concentration of Metal-Complexing Agent (mM) | % Release of 1-MCP |
|---|---|---|
| tetrasodium pyrophosphate | 1 | 42 |
| tetrasodium pyrophosphate | 5 | 39 |
| tetrasodium pyrophosphate | 10 | 54 |
| sodium carbonate | 1 | 61 |
| sodium carbonate | 5 | 68 |
| sodium carbonate | 10 | 71 |
| nitrilotriacetic acid | 1 | 97 |
| nitrilotriacetic acid | 5 | 100 |
| nitrilotriacetic acid | 10 | 95 |
| Tartaric acid | 1 | 99 |
| Tartaric acid | 5 | 85 |
| Tartaric acid | 10 | 92 |
| Poly(acrylic acid)[2] | 0.1 | 20 |
| Poly(acrylic acid)[2] | 0.5 | 60 |
| Poly(acrylic acid)[2] | 1 | 54 | note
[2] molecular weight 2000.

All of the metal-complexing agents, if used in sufficient quantity, maintain the activity of 1-MCP as compared to the control sample from Example 4 (deionized water with 5 ppm copper ion and no metal-complexing agent), which had 1-MPC release of 36%.

Example 6

Tomato Epinasty Testing

Tomato epinasty tests were performed as follows:
Tomatoes (Rutgers 39 Variety Harris Seeds No 885 Lot 37729-A3) were grown in 2½" square pots filled with a commercial potting mix. Two seeds were place in each pot. Plants that had expanded first true leaves and were between 3 and 5 inches high were used for the tomato epinasty test.

To conduct the assay, the plants were sprayed to run off with the test 1-MCP foliar spray and allowed to dry for 4 hours in sunlight These operations were performed in a ventilated area away from the plants growing in the greenhouse so there would not be any unintended treatment to growing plants destined for later experiments.

The 1-MCP treated plants and both treated and untreated controls were placed into an SLX controlled-atmosphere shipping box and sealed. To the box, ethylene was injected through a septum, which gave a concentration of 14 ppm. The plants were held sealed for 12-14 hours in the dark with ethylene in the atmosphere. At the end of ethylene treatment, the box was opened and scored for epinasty. Scoring for epinasty was accomplished by using the following scoring system for each pot.
1. 0% no epinasty (100% control)
2. 20% A couple leaves show some drooping (80% control)
3. 50% Plants show 50% of full response. Not all leaves need to show effect. (50% control)
4. 80% Almost all leaves drooping and some show underside of leaf exposed on top. (20% control)
5. 100% Leaves completely drooping and the underside of the leaf exposed from above. (0% control)

The score of each pot is recorded. The average of 6 or 8 pots is averaged to get a score. The percentage improvement is calculated by interpolating the percentage improvement from the control water (i.e., no additives) 1-MCP treatment.

Tomato epinasty tests were conducted using a formulation that included water; a 1-MCP α-CD complex that contained 0.14% 1-MCP by weight, based on the weight of the 1-MCP α-CD complex; and sodium salt of EDTA. The amount of 1-MCP α-CD complex was chosen so that the formulation had 140 ppb of 1-MCP. The amount of sodium salt of EDTA varied, as shown in the table below. Also included in the formulation were an anionic surfactant (0.1% by weight based on the weight of the formulation), isopropanol (1% by weight based on the weight of the formulation), and a spray oil (1% by weight based on the weight of the formulation). Results were as follows:

| Water Source | 1-MCP Concentration (ppb) | EDTA Concentration (mM) | % Control of Epinasty |
|---|---|---|---|
| De-ionized water (C) | 0 | 0 | 0 |
| De-ionized water (C) | 140 | 0 | 100 |
| Well Water (C) | 140 | 0 | 0 |
| Well Water | 140 | 0.003 | 80 | deionized water alone does not control epinasty; deionized water with 1-MCP does control epinasty; well water with 1-MCP does not control epinasty; well water with 1-MCP and sodium salt of EDTA (a composition of the present invention) does control epinasty.

We claim:
1. A sprayable liquid composition comprising:
at least one cyclopropene of the formula (1)

$$R-C{\overset{CH}{\underset{CH_2}{\diagdown}}} \quad (1)$$

wherein R is selected from the group consisting of hydrogen, an unsubstituted alkyl, alkenyl, alkynyl, cycloalkyl, cycloalkylalkyl, phenyl, or naphthyl group, and a substituted alkyl, alkenyl, alkynyl, cycloalkyl, cycloalkylalkyl, phenyl, or naphthyl group having as a substitutent a halogen, alkoxy, substituted phenoxy, or unsubstituted phenoxy group;

at least molecular encapsulating agent that encapsulates the cyclopropene;

at least one metal complexing agent selected from the group consisting of ethylenediaminetetraacetic acid (EDTA), hydroxyethylethylenediaminetriacetic acid, nitrilotriacetic acid, N-dihydroxyethylglycine, and ethylenebis(hydroxyphenylglycine); and water.

2. The liquid composition of claim 1, wherein the metal complexing agent is EDTA.

3. The liquid composition of claim 2, wherein the composition further comprises an alkaline carbonate.

4. The liquid composition of claim 3, wherein the alkaline carbonate is sodium carbonate.

5. A method for blocking the effects of ethylene or plant part, the method comprising contacting the liquid composition of claim 1 to the plant or plant part.

6. The method according to claim 5, wherein contacting the liquid composition to the plant or plant part comprises spraying, foaming, fogging, pouring, brushing, or dipping.

7. The method according to claim 6, wherein contacting the liquid composition to the plant or plant part comprises dipping.

8. The method according to claim 6, wherein contacting the liquid composition to the plant or plant part comprises spraying.

9. The liquid composition of claim 1, wherein the amount of the cyclopropene(s) in the composition is between 1 ppb and 1,000 ppm.

10. The liquid composition of claim 1, wherein the metal complexing agent is in a complex with one or more metal ions.

11. A method for blocking the effects of ethylene in a plant or plant part, the method comprising:
    contacting the liquid composition of claim 9 to the plant or plant part.

12. The liquid composition of claim 9, wherein the metal complexing agent is in a complex with one or more metal ions.

13. The liquid composition of claim 10, wherein the composition comprises metal complexing agent in a complex with iron ions.

14. The liquid composition of claim 10, wherein the composition comprises metal complexing agent in a complex copper ions.

15. The method according to claim 6, wherein contacting the composition to the plant or plant part comprises spraying and dipping.

16. The method according to claim 5, wherein contacting the composition to the plant or plant part is performed in a ventilated area.

17. A method for blocking the effects of ethylene in a plant or plant part, the method comprising:
    contacting the liquid composition of claim 10 to the plant or plant part.

18. A method for blocking the effects of ethylene in a plant or plant part, the method comprising:
    contacting the liquid composition of claim 12 to the plant or plant part.

19. The method according to claim 5, wherein when contacting the liquid composition to the plant or plant part, cyclopropene is released from the molecular encapsulating agent in an amount greater than is released upon contact with a plant or plant part of an otherwise identical composition that does not comprise the metal complexing agent.

20. The method according to claim 5, wherein substantially all of the cyclopropene is released from the molecular encapsulating agent when the liquid composition contacts the plant or plant part.

21. The liquid composition of claim 1, wherein the metal complexing agent is present in an amount of 1% by weight or less of the composition.

22. The liquid composition of claim 1, wherein the metal complexing agent is present in an amount of 0.01% by weight or more of the composition.

* * * * *